United States Patent [19]

Mack et al.

[11] Patent Number: Plant 6,404

[45] Date of Patent: Nov. 15, 1988

[54] CHRYSANTHEMUM PLANT NAMED LEGEND

[75] Inventors: Grace H. Mack, 108 Wahackme Rd., New Canaan, Conn. 06840; Cornelis P. VandenBerg, Salinas, Calif.

[73] Assignee: Grace H. Mack, New Canaan, Conn.

[21] Appl. No.: 939,478

[22] Filed: Dec. 8, 1986

[51] Int. Cl.[4] ..... A01H 5/00

[52] U.S. Cl. ..... Plt./78

[58] Field of Search ..... Plt./78

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Legend particularly characterized by its flat capitulum form; decorative capitulum type; yellow ray floret color; diameter across face of capitulum of up to 4 cm at maturity; medium plant height with spreading and prolific branching pattern; average natural season flower date of August 22 in Salinas, Calif. and September 17 in Hightstown, N.J.; uniform seven week photoperiodic flowering response to short days in photoperiodic controlled flowering programs; and by its durable, uniform performance in outside fall flowerings and in spring small pot flowering programs.

3 Drawing Sheets

The present invention comprises a new and distinct cultivar of chrysanthemum, botanically known as *Chrysanthemum morifolium,* Ramat., and referred to by the cultivar name Legend.

Legend, identified as 82M18023, was originated from a cross made by Grace H. Mack in a controlled breeding program in New Canaan, Conn., in 1981. The parents of Legend were both unnamed seedlings.

Legend was discovered and selected as one flowering plant within the progeny of the stated cross by Cornelis P. VandenBerg in September 1982, in a controlled environment in Salinas, Calif.

The first act of asexual reproduction of Legend was accomplished when vegetative cuttings were taken from the initial selection in December 1982 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Legend are firmly fixed and are retained through successive generations of asexual reproduction.

Legend has not been observed under all possible environmental conditions. The phenotype may vary significantly with variations in environment such as temperature, light intensity, and daylength.

The following observations, measurements and comparisons describe plants grown in controlled open areas in Salinas, Calif. and in Hightstown, N.J. Rooted cuttings were established in soil and maintained outdoors under the natural temperature and daylength prevailing during July through September. Single pinching was practiced with all branches and buds retained.

The following traits have been repeatedly observed and are determined to be basic characteristics of Legend, which, in combination, distinguish this Chrysanthemum as a new and distinct cultivar:

1. Flat capitulum form.
2. Decorative capitulum type.
3. Yellow ray floret color.
4. Diameter across face of capitulum up to 4 cm at maturity.
5. Medium plant height.

6. Spreading and prolific branching pattern.
7. Average natural season flower date of August 22 in Salinas, Calif., and September 17 in Hightstown, N.J.
8. Uniform seven week photoperiodic flowering response to short days in photoperiodic controlled flowering programs.
9. Durable, uniform performance in outside fall flowerings and in spring small pot flowering programs.

The accompanying photographic drawings show typical inflorescence and leaf characteristics of Legend, with the colors being as nearly true as possible with illustrations of this type.

Sheet 1 is a color photograph of Legend grown as a pinched spray pot mum.

Sheet 2 is a black and white photograph of three views of the inflorescence of Legend.

Sheet 3 is a black and white photograph showing the upper and under sides of the leaves of Legend at three stages of development (mature, intermediate and immature).

Of the commercial cultivars known to the inventors, the most similar in comparison to Legend is Goldmine, disclosed in U.S. Plant Pat. No. 5,661. Reference is made to attached Chart A, which compares certain characteristics of Legend to the same characteristics of Goldmine.

Similar traits are ray floret color, capitulum type and controlled flowering response. The capitulum form of Legend is more flat, with a slightly smaller diameter across face of capitulum than Goldmine. Legend has more vigor, a more uniform response, and an earlier response than Goldmine in natural season fall flowerings.

In the following description, color references are made to The Royal Horticultural Society Color Chart. The color values were determined on plant material grown outside in Salinas, Calif. on Aug. 25, 1986.

Classification:

*Botanical.*—*Chrysanthemum morifolium,* Ramat., cv. Legend.

*Commercial.*—Decorative spray pot mum and garden mum.

INFLORESCENCE

A. Capitulum:

*Form.*—Flat.

*Type.*—Decorative.

*Diameter across face.*—Up to 4 cm at maturity.

B. Corolla of ray florets:

*Color (general tonality from a distance of three meters).*—Yellow.

*Color (upper surface).*—12A to 13A.

*Color (under surface).*—12B to 13B.

*Shape.*—Oblong.

C. Corolla of disc florets:

*Color (mature).*—3A.

*Color (immature).*—154B.

D. Reproductive organs:

*Androecium.*—Present on disc florets only, very few; scant pollen.

*Gynoecium.*—Present on both ray and disc florets.

PLANT

A. General appearance:

*Height.*—Medium.

*Branching pattern.*—Spreading and prolific.

B. Foliage:

*Color (upper surface).*—137A to 137B.

*Color (under surface).*—137B to 137C.

*Shape.*—Lobed and slightly serrated.

CHART A

COMPARISON OF LEGEND AND GOLDMINE

| CULTIVAR | RAY FLORET COLOR | CAPITULUM FORM AND TYPE | BRANCHING PATTERN |
|---|---|---|---|
| LEGEND | YELLOW | FLAT | SPREADING |
| GOLDMINE | YELLOW | DECORATIVE ROUND POMPON DECORATIVE | AND PROLIFIC SPREADING |

CHART A-continued

COMPARISON OF LEGEND AND GOLDMINE

| CULTIVAR | DIAMETER ACROSS FACE OF CAPITULUM | PLANT HEIGHT | AVERAGE NATURAL SEASON FLOWER DATE SALINAS, CALIFORNIA |
|---|---|---|---|
| LEGEND | UP TO 4 cm. | MEDIUM | AUGUST 22 |
| GOLDMINE | UP TO 4.5 cm. | SHORT | AUGUST 27 |

| CULTIVAR | AVERAGE NATURAL SEASON FLOWER DATE HIGHTSTOWN NEW JERSEY | CONTROLLED RESPONSE |
|---|---|---|
| LEGEND | SEPTEMBER 17 | 7 WEEKS |
| GOLDMINE | SEPTEMBER 20 | 7 WEEKS |

COMPARISONS MADE OF PLANTS GROWN UNDER CONTROLLED OUTSIDE CONDITIONS IN SALINAS, CALIFORNIA AND IN HIGHTSTOWN, NEW JERSEY.

We claim:

1. A new and distinct Chrysanthemum plant named Legend, as described and illustrated, and particularly characterized as to uniqueness by the combined characteristics of flat capitulum form; decorative capitulum type; yellow ray floret color; diameter across face of capitulum of up to 4 cm at maturity; medium plant height with spreading and prolific branching pattern; average natural season flower date of August 22 in Salinas, Calif. and September 17 in Hightstown, N.J.; uniform seven week photoperiodic flowering response to short days in photoperiodic controlled flowering programs; and durable, uniform performance in outside fall flowerings and in spring small pot flowering programs.

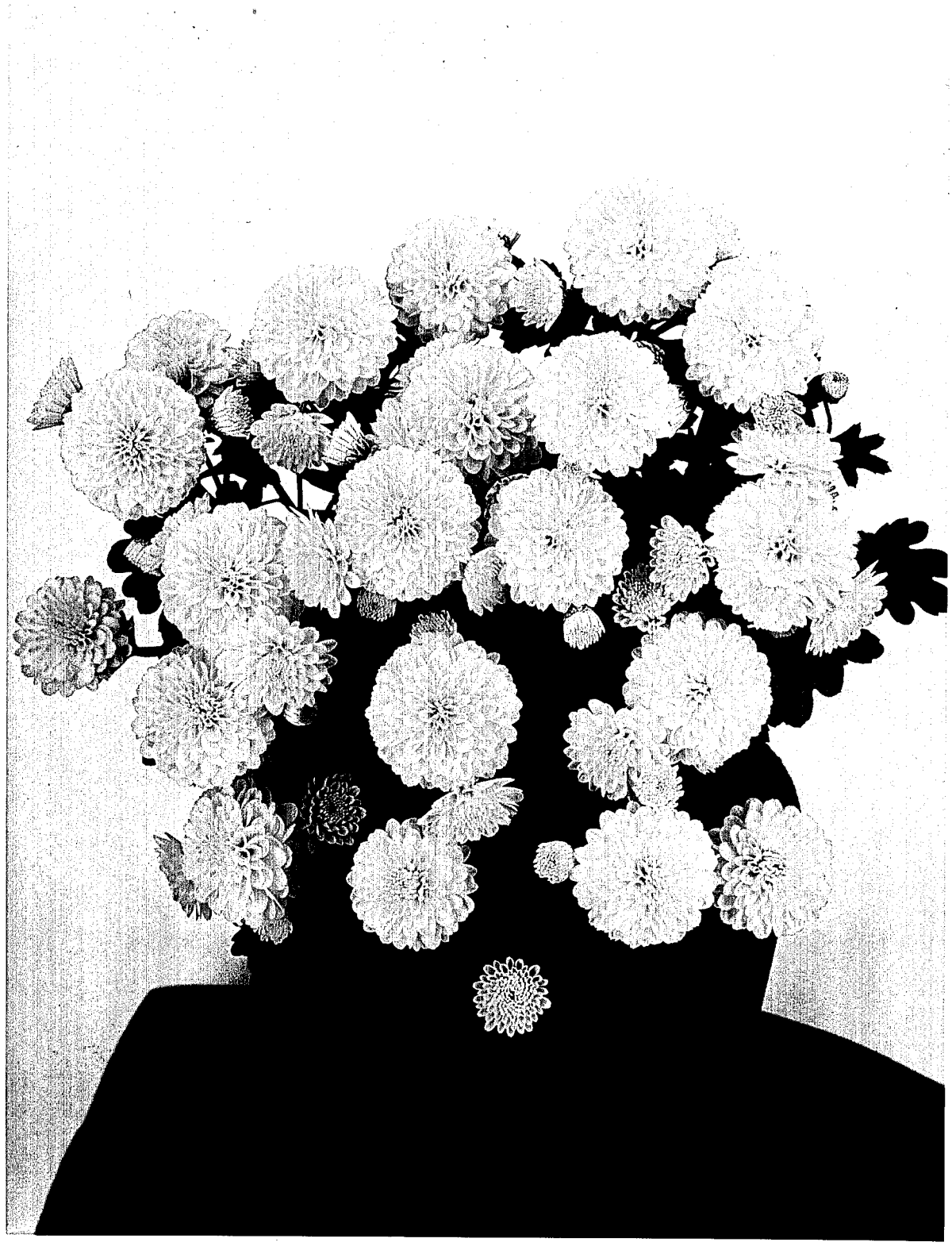

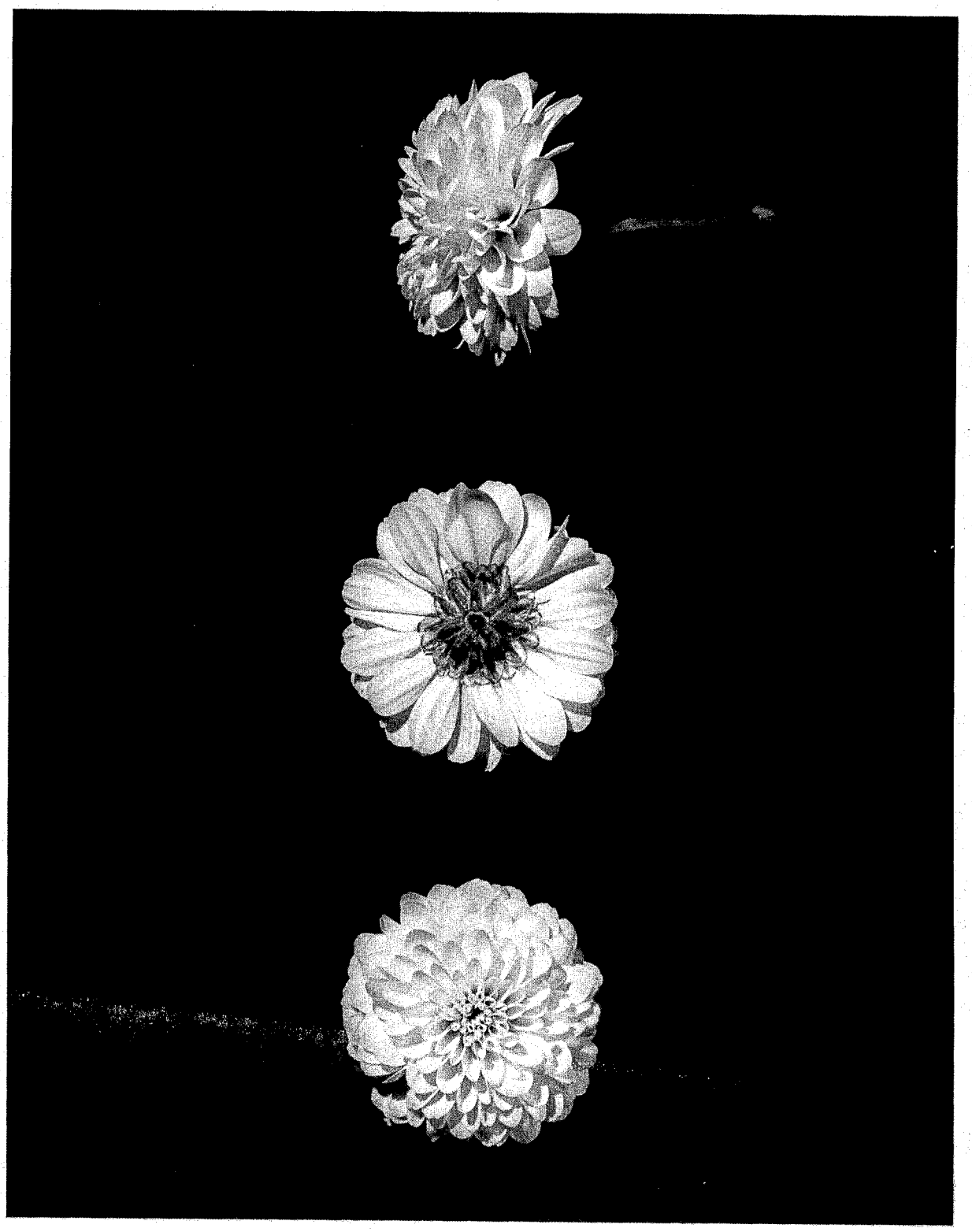

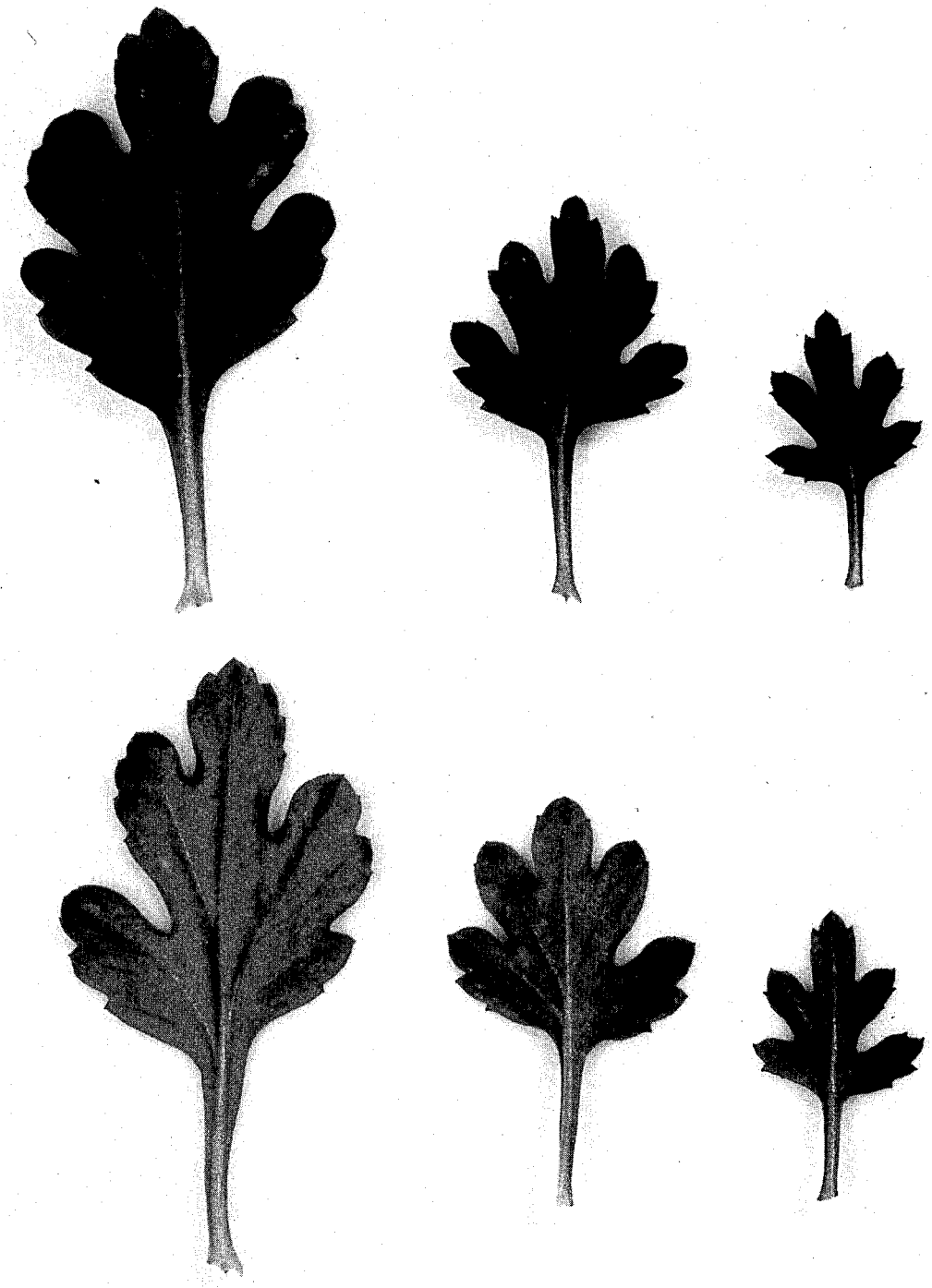

* * * * *